(12) United States Patent
Mueller

(10) Patent No.: US 7,781,221 B2
(45) Date of Patent: Aug. 24, 2010

(54) SYSTEM AND METHOD OF COMPENSATING FOR SYSTEM DELAY IN ANALYTE ANALYZATION

(75) Inventor: Cord Mueller, Middletown, CT (US)

(73) Assignee: RIC Investments, LLC, Wilmington, DE (US)

( * ) Notice: Subject to any disclaimer, the term of this patent is extended or adjusted under 35 U.S.C. 154(b) by 0 days.

(21) Appl. No.: 11/837,907

(22) Filed: Aug. 13, 2007

(65) Prior Publication Data

US 2008/0044922 A1 Feb. 21, 2008

Related U.S. Application Data

(60) Provisional application No. 60/838,806, filed on Aug. 18, 2006.

(51) Int. Cl.
*G01N 21/64* (2006.01)
*G01N 21/00* (2006.01)
*B01J 19/08* (2006.01)
*B01J 19/00* (2006.01)

(52) U.S. Cl. ............... 436/127; 436/164; 436/172; 422/83; 422/50

(58) Field of Classification Search .......... 436/127; 422/84; 324/76.24; 128/633; 600/310
See application file for complete search history.

(56) References Cited

U.S. PATENT DOCUMENTS

| | | | |
|---|---|---|---|
| 4,716,363 A | 12/1987 | Dukes et al. | |
| 5,348,003 A * | 9/1994 | Caro | ............... 600/310 |
| 6,616,896 B2 | 9/2003 | Labuda et al. | |
| 6,632,402 B2 | 10/2003 | Blazewicz et al. | |

* cited by examiner

*Primary Examiner*—Walter D Griffin
*Assistant Examiner*—Christine T Mui

(57) ABSTRACT

A system configured to determine information related to one or more gaseous analytes in a body of gas comprises a luminescable material, one or more emitters, one or more photosensitive detectors, and a processor. The emitters emit amplitude modulated electromagnetic radiation onto the luminescable medium in communication with a body of gas causing luminescence in the luminescable medium. The photosensitive detectors receive the amplitude modulated electromagnetic radiation generated by the luminescence of the luminescable medium and generate one or more output signals, at least one of the output signals indicating the intensity of the received electromagnetic radiation. The processor receives the output signals and determines information related to one or more gaseous analytes in the body of gas. The determination of information related to the one or more gaseous analytes may comprise compensating for a delay that varies as a function of the intensity of the received electromagnetic radiation.

23 Claims, 4 Drawing Sheets

SYSTEM AND METHOD OF COMPENSATING FOR SYSTEM DELAY IN ANALYTE ANALYZATION

CROSS-REFERENCE TO RELATED APPLICATIONS

This application claims priority under 35 U.S.C. §119(e) from provisional U.S. patent application No. 60/838,806 filed Aug. 18, 2006 the contents of which are incorporated herein by reference.

BACKGROUND OF THE INVENTION

1. Field of the Invention

The invention relates generally to a system and method that determine information related to one or more gaseous analytes in a body of gas, and more particularly to adjusting for inaccuracies in the determination of such information.

2. Description of the Related Art

The use of luminescence-quenching detection to determine information related to gaseous analytes present in a body of gas is known. However, conventional systems may not adequately compensate for certain systematic errors introduced by their componentry. For example, photosensitive detectors are generally used by conventional systems to detect luminescence from a luminescable medium. The photosensitive detectors may introduce system delays that are not adequately compensated for by the conventional systems. Other system components (such as and without limitation, amplifiers and filters) may also introduce delay. These system delays may lead to inaccurate and/or imprecise determinations of information related to the gaseous analytes.

SUMMARY OF THE INVENTION

One aspect of the invention relates to a system configured to determine information related to one or more gaseous analytes in a body of gas. In one embodiment the system comprises one or more emitters, one or more photosensitive detectors, and a processor. The one or more emitters are configured to emit amplitude modulated electromagnetic radiation onto a luminescable medium in communication with a body of gas, wherein the electromagnetic radiation emitted by the emitter onto the luminescable medium causes luminescence in the luminescable medium. The photosensitive detectors are configured to receive electromagnetic radiation that is generated by the luminescence of the luminescable medium, wherein the one or more photosensitive detectors generate one or more output signals in response to the received electromagnetic radiation, the output signals indicating an intensity of the received electromagnetic radiation. The processor is adapted to receive the one or more output signals generated by the photosensitive detectors and adapted to determine information related to one or more gaseous analytes in the body of gas based on a phase difference between a modulation of the amplitude of the emitted amplitude modulated electromagnetic radiation and a modulation of the amplitude of the received amplitude modulated electromagnetic radiation. In one embodiment, the determination of information related to the one or more gaseous analytes by the processor comprises compensating for a delay by the one or more photosensitive detectors in the generation of the one or more output signals, the compensation varying as a function of the intensity of the received amplitude modulated electromagnetic radiation.

Another aspect of the invention relates to a method of determining information related to one or more gaseous analytes in a body of gas. In one embodiment the method comprises providing an emitted amplitude modulated electromagnetic radiation onto a luminescable medium in communication with a body of gas so as to cause luminescence in the luminescable medium; receiving an amplitude modulated electromagnetic radiation that is generated by the luminescence of the luminescable medium; generating one or more output signals indicating an intensity of the received amplitude modulated electromagnetic radiation received from the luminescable medium; determining information related to one or more gaseous analytes in the body of gas based on a phase difference between a modulation of the amplitude of the emitted amplitude modulated electromagnetic radiation provided to the luminescable medium and a modulation of the amplitude of the received amplitude modulated electromagnetic radiation; and providing a compensation for a delay between the receipt of the received amplitude modulated electromagnetic radiation and the generation of the one or more output signals, the compensation varying as a function of the intensity of the received amplitude modulated electromagnetic radiation.

Yet another aspect of the invention relates to a processor configured to determine information related to one or more gaseous analytes in a body of gas. In one embodiment, the processor comprises a phase difference module, a delay compensation module, and an analyte information module. The phase difference module is adapted to determine a phase difference between (i) a modulation of the amplitude of an emitted amplitude modulated electromagnetic radiation that has been provided to a luminescable medium in communication with a body of gas, and (ii) a modulation of the amplitude of a received amplitude modulated electromagnetic radiation generated by luminescence of the luminescable medium in response to the emitted amplitude modulated electromagnetic radiation provided thereon. In some instances, the phase difference module is adapted to determine the phase difference based on one or more output signals generated by a photosensitive detector that is structured to receive at least a portion of the received amplitude modulated electromagnetic radiation generated by the luminescence of the luminescable medium, the photosensitive detector generating the one or more output signals to indicate at least the intensity of the received amplitude modulated electromagnetic radiation. The delay compensation module is adapted to compensate for a delay of the photosensitive detector in generating the one or more output signals, wherein the compensation performed by the delay compensation module varies as a function of the intensity of the received amplitude modulated electromagnetic radiation. The analyte information module is adapted to determine information related to one or more gaseous analytes in the body of gas based on the phase difference.

Yet another aspect of the invention relates to a method of determining information on a gaseous analyte in a body of gas. In one embodiment, the method comprises determining a phase difference between (i) a modulation of the amplitude of an emitted amplitude modulated electromagnetic radiation provided to a luminescable medium in communication with a body of gas and (ii) a modulation of the amplitude of a received amplitude modulated electromagnetic radiation generated by the luminescence of the luminescable medium, wherein the phase difference is determined, at least in part, based on output signals generated as a function of the intensity of the received amplitude modulated electromagnetic radiation generated by the luminescence of the luminescable medium; compensating for a delay in generation of the output signals as a function of the intensity of the received amplitude modulated electromagnetic radiation generated by the luminescence of the luminescable medium; and determining information related to the gaseous analyte based upon the determining and the compensating.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise

DETAILED DESCRIPTION OF THE EXEMPLARY EMBODIMENTS

Figure 1:
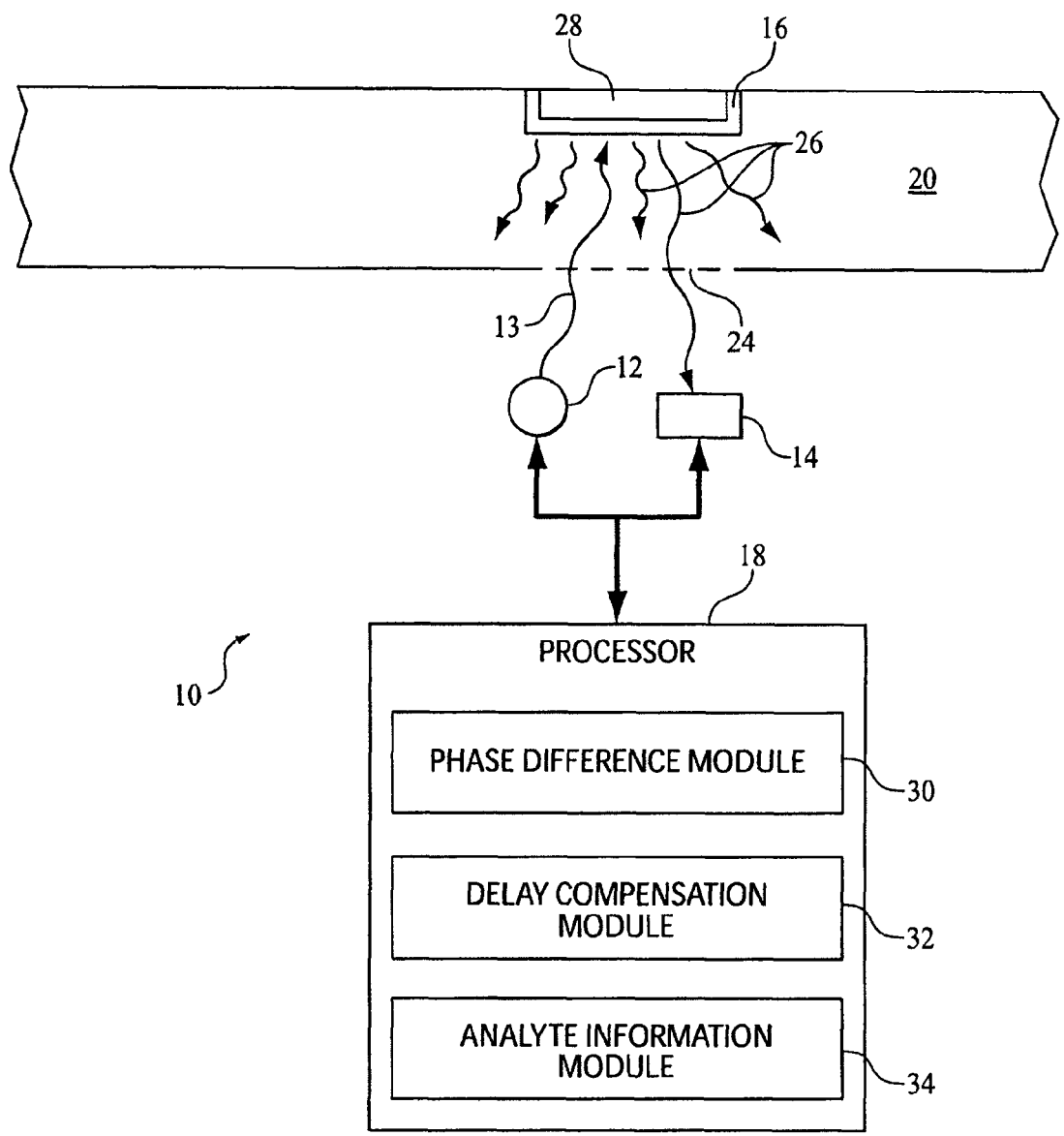
FIG. 1 illustrates a system configured to determine information related to one or more gaseous analytes in a body of gas, in accordance with one embodiment of the invention.

FIG. 1 illustrates a system 10 configured to determine information related to one or more gaseous analytes in a body of gas. System 10 includes one or more emitters 12, a photosensitive detector 14, a luminescable medium 16, and a processor 18. System 10 may determine information related to one or more gaseous analytes in the body of gas contained within a flow path 20. In one example, flow path 20 is defined by a conduit 22 adapted to carry gas to and/or from a patient. In a more particular example, conduit 22 may cooperate with a patient interface appliance configured to communicate with an airway of the patient. Some examples of the patient interface appliance may include, for example, an endotracheal tube, a nasal canula, a tracheotomy tube, a mask, or other patient interface appliances. The present invention is not limited to these examples, and contemplates determination of analytes in any body of gas.

In some implementations, emitter 12, photosensitive detector 14, and/or luminescable medium 16 may form a sensor. The sensor may be formed as a single unit for integration with conduit 22 and/or an airway adapter (not shown) structured to couple with conduit 22. For example, U.S. Pat. No. 6,616,896 to Labuda et al., entitled "OXYGEN MONITORING APPARATUS," and issued Sep. 9, 2003 (hereafter "the '896 patent"), and U.S. Pat. No. 6,632,402 to Blazewicz et al., entitled "OXYGEN MONITORING APPARATUS," and issued Oct. 14, 2003 (hereafter "the '402 patent") both describe sensors that (1) include components similar to some or all of emitter 12, photosensitive detector 14, and/or luminescable medium 16, and (2) determine information related to one or more gaseous analytes in a body of gas. Both of these patents are hereby incorporated, in their entireties, into this disclosure by reference.

Emitter 12 emits electromagnetic radiation, indicated by wavy line 13 that is directed onto luminescable medium 16. As will be discussed further below, electromagnetic radiation 13 emitted by emitter 12 includes electromagnetic radiation with a wavelength that causes luminescable medium 16 to luminesce. Emitter 12 may include one or more Organic Light Emitting Diodes ("OLEDs"), lasers (e.g., diode lasers or other laser sources), Light Emitting Diodes ("LEDs"), Hot Cathode Fluorescent Lamps ("HCFLs"), Cold Cathode Fluorescent Lamps ("CCFLs"), incandescent lamps, halogen bulbs, received ambient light, and/or other electromagnetic radiation sources.

In one implementation, emitter 12 includes one or more green and/or blue LEDs. These LEDs typically have high intensity in the luminescable composition absorption region of luminescable medium 16 and output smaller amounts of radiation at other wavelengths (e.g., UV and/or near-UV). This minimizes stray interfering light and photo-degradation of the sensor formed by emitter 12, photosensitive detector 14, and/or luminescable medium 16.

While the present invention is by no means limited to the use of LEDs, other advantages of implementing LEDs as emitter 12 include their light weight, compactness, low power consumption, low voltage requirements, low heat production, reliability, ruggedness, relatively low cost, and stability. Also LEDs can be switched on and off very quickly, reliably, and reproducibly.

In some implementations, system 10 may include one or more optical elements (not shown) to guide, focus, and/or otherwise process radiation 13 emitted by emitter 12. For example, one or more lenses may collimate radiation 13 in a selected direction. As more particular examples, both of the incorporated '896 and '402 patents disclose the use of optical elements that process radiation emitted by an emitter similar to emitter 12.

Electromagnetic radiation 13 from emitter 12 may arrive at luminescable medium 16 with a predetermined amplitude modulation (e.g., having a predetermined frequency, having a predetermined maximum and/or minimum amplitude, etc.). In one embodiment, emitter 12 may be driven to emit electromagnetic radiation 13 with the predetermined amplitude modulation. In another embodiment, system 10 may include one or more optical elements (not shown) that modulate the amplitude of electromagnetic radiation emitted 13 by emitter 12. The one or more optical elements may include one or more periodically driven active elements (e.g., a liquid crystal stack, etc.) and/or one or more passive elements that are periodically moved into and out of an optical path of electromagnetic radiation 13 emitted by emitter 12 (e.g., filters, half-mirrors, etc.).

As can be seen in FIG. 1, conduit 22 may include a window 24. Window 24 may be substantially transparent to enable electromagnetic radiation, such as electromagnetic radiation 13 emitted by emitter 12, to enter and/or exit the interior of conduit 22. For instance, window 24 may be formed of sapphire, one or more polymers (e.g., polyethylene, etc.), a glass, and/or other substantially transparent materials. In some embodiments (not shown), conduit 22 may include two windows similar to window 24. As is shown and described in the '402 reference, the two windows may be disposed in an airway adapter opposite from each other to enable electromagnetic radiation 13 to pass through the airway adapter. In this arrangement, photosensitive detector 14 may be positioned on an opposite side from emitter 12.

Luminescable medium 16 is a medium that, in response to exposure to electromagnetic radiation 13 from emitter 12 and/or some other excitation energy, luminesces to emit electromagnetic radiation, indicated by wavy lines 26, in a substantially omni-directional manner at a wavelength different from that of electromagnetic radiation 13 provided by emitter 12. The intensity and/or persistence of this luminescent electromagnetic radiation 26 rises and falls according to the relative amounts of one or more analytes included in the body of gas within conduit 22. In one embodiment, oxygen causes a modification of the intensity and/or persistence of luminescent electromagnetic radiation 26 by quenching the luminescence reaction. As the concentration of oxygen increases, the modification of the intensity and/or persistence of luminescent electromagnetic radiation 26 will decrease. In one embodiment, luminescable medium 16 is formed as a luminescent film. For example, both of the incorporated '896 and '402 patents disclose films that may be employed as luminescable medium 16.

In the embodiment illustrated in FIG. 1, luminescable medium 16 is disposed on a thermal capacitor 28. Thermal capacitor 28 is employed to maintain luminescable medium 16 at a substantially constant operating temperature and thereby reduce or eliminate inaccuracies in system 10 attributable to variations in the temperature of luminescable medium 16.

Photosensitive detector 14 is positioned to receive at least a portion of luminescent electromagnetic radiation 26 from luminescable medium 16. Accordingly, luminescent electromagnetic radiation 26 may also be referred to as "received electromagnetic radiation 26", or the like, herein. Based on the received electromagnetic radiation 26, photosensitive detector 14 generates one or more output signals related to one or more properties of received electromagnetic radiation 26. For example, the one or more output signals may be related to an amount of received electromagnetic radiation 26, an intensity of received electromagnetic radiation 26, a modulation of the amplitude of received electromagnetic radiation 26, and/or other properties of received electromagnetic radiation 26. In one embodiment, photosensitive detector 14 includes a PIN diode. In other embodiments, other photosensitive devices are employed as photosensitive detector 14. For instance, photosensitive detector 14 may take the form of a diode array, a CCD chip, a CMOS chip, a photomultiplier tube (PMT) and/or other photosensitive devices.

In generating the one or more output signals, photosensitive detector 14 may introduce a delay into system 10. It should be noted that the term "delay" as used herein refers to a lag between the reception of a given photon of received electromagnetic radiation 26 at photosensitive detector 14 and the generation of an output signal that includes information related to the reception of the given photon on photosensitive detector 14. For simplicity, "delay" is discussed herein in conjunction with photosensitive detector 14; however, it is contemplated that delay may also be introduced by other system components (such as, and without limitation, amplifiers and filters) which are used to generate an output signal. In some instances, this delay may not be constant. For example, the delay may vary as a function of the intensity (e.g., the amplitude) of luminescent electromagnetic radiation 26 received by photosensitive detector 14. In some instances, the delay increases as the intensity of luminescent electromagnetic radiation 26 decreases. For various reasons, some of which are discussed below, system 10 may compensate for this delay in order to enhance the precision and/or accuracy of the determination of information related to one or more gaseous analytes in the body of gas contained in conduit 22.

In the current embodiment, photosensitive detector 14 is calibrated to compensate for the delay described above. The calibration of photosensitive detector 14, for example, may include taking a series of calibration measurements of the delay of photosensitive detector 14 at a plurality of intensities, or at least a single intensity in another embodiment. The measured delays and the corresponding measured intensities obtained during the calibration measurements may then used to determine a compensation curve that describes the delay of photosensitive detector 14 as a function of measured intensity. For instance, in one embodiment, a curve-fitting algorithm is used to fit the measured delays and the corresponding measured intensities to a compensation curve of the form $D=a+b \cdot I+c/I$, where D represents the measured delay, I represents the corresponding measured intensity, and a, b, and c represent constant coefficients determined by the curve-fitting algorithm. It should be appreciated that this form of the compensation curve is provided for illustrative purposes and that other forms may be used. For example, a higher order polynomial may be used, a trigonometric function may be used, etc.

It should further be appreciated that the implementation of a calibration curve is only one of a variety of possible mechanisms that can be used as compensation for the delay of photosensitive detector 14. For example, a look-up table may be created that provides values for the system delay of photosensitive detector 14 that correspond to various measured intensities.

The calibration of photosensitive detector 14 to determine a compensation curve may be performed when the sensor including photosensitive detector 14 is produced. In some embodiments, this initial compensation curve determined during this initial calibration is used for the lifetime of photosensitive detector 14. In other embodiments, photosensitive detector 14 is re-calibrated periodically to determine an updated compensation curve.

Figure 2:
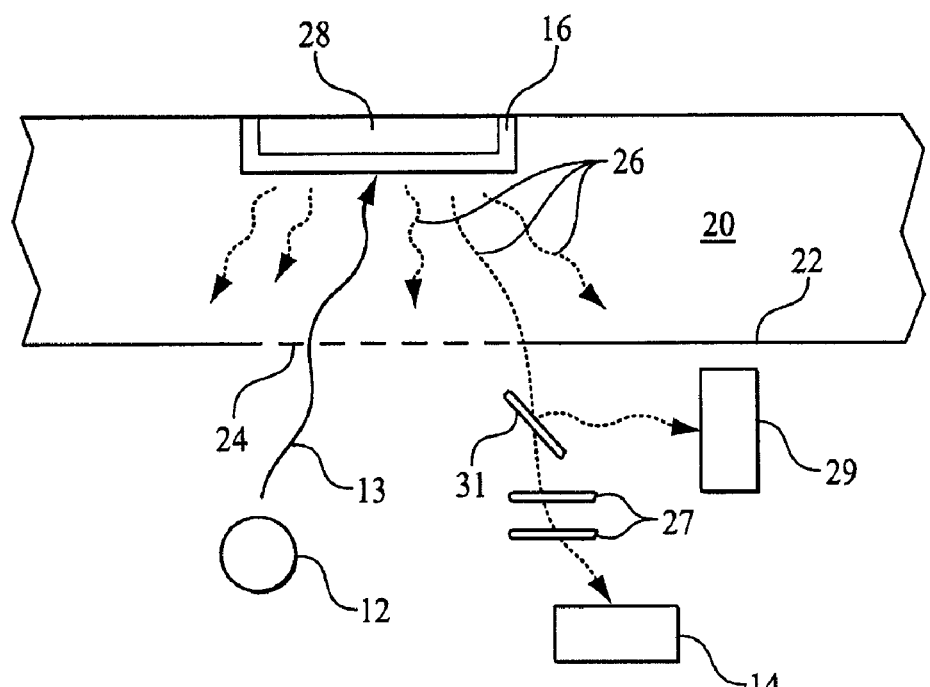
FIG. 2 illustrates a sensor including a photosensitive detector, in accordance with one embodiment of the invention.

FIG. 2 illustrates an embodiment of the sensor including photosensitive detector 14 in which one or more filter elements 27 are positioned between luminescable medium 16 and photosensitive detector 14. As is described in both the incorporated '896 and '402 patents, filter elements 27 are typically designed to prevent electromagnetic radiation not emitted by luminescable medium 16 from becoming incident on photosensitive detector 14. For instance, in one embodiment, filter element 27 are wavelength specific and permit luminescent radiation 26 to pass through to become incident on photosensitive detector 14 while substantially blocking radiation with other wavelengths.

This embodiment of the sensor also includes a reference photosensitive detector 29 and a beam splitting element 31. As is described in the incorporated '896 patent, beam splitting element 31 may direct a portion of radiation 26 propagating toward photosensitive detector 14 onto reference photosensitive detector 29. One or more output signals generated by reference photosensitive detector 29 may be used as a reference to account, and compensate, for system noise (e.g., intensity fluctuations in emitter 12, etc.) in the one or more output signals generated by photosensitive detector 14.

Figure 3:
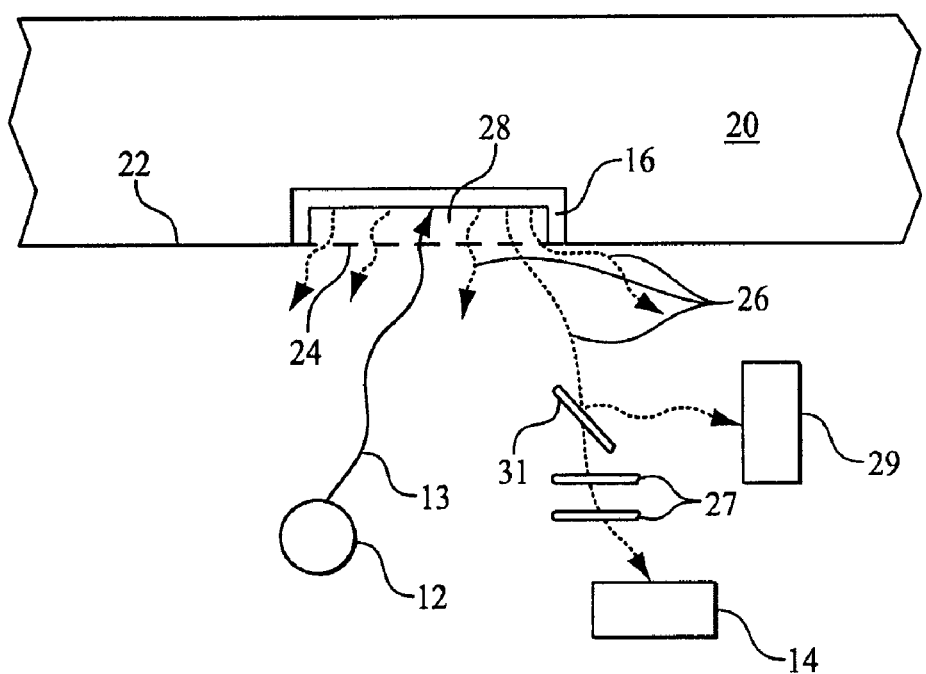
FIG. 3 illustrates a sensor including a photosensitive detector, in accordance with one embodiment of the invention.

FIG. 3 illustrates yet another configuration of the sensor. In the configuration illustrated in FIG. 3, thermal capacitor 28 is at least partially transparent, and is located adjacent to window 24. In this configuration luminescable medium 16 is disposed on thermal capacitor 28 on an opposite side of capacitor 28 from window 24. Luminescable medium 16 is exposed to flow path 20 on a side of luminescable medium 16 that is opposite the boundary between capacitor 28 and luminescable medium 16. As can be seen, electromagnetic radiation 13 emitted by emitter 12 passes through both window 24 and thermal capacitor 28 to become incident on luminescable medium 16. Luminescent radiation 26 emitted from luminescable medium 16 proceeds back through thermal capacitor 28 and window 24 to become incident on one or both of photosensitive detectors 14 and/or 29, in substantially the same manner as is described above.

Returning to FIG. 1, in one embodiment, one or more gaseous analytes present in the body of gas at luminescable medium 16 quench the luminescence exhibited by luminescable medium 16 in response to receiving radiation 13 from emitter 12. More particularly, the peak luminescence and decay time of the luminescence exhibited by luminescable medium 16 decreases as the amount of these one or more gaseous analytes present at luminescable medium 16 increases. In one embodiment, the one or more gaseous analytes may include oxygen.

Processor 18 is operatively coupled with emitter 12 and photosensitive detector 14. Processor 18 is configured to determine information about one or more gaseous analytes in a body of gas within conduit 22. Processor 18 determines this information based on known and/or measured information related to (1) the emission of electromagnetic radiation 13 by emitter 12 onto luminescable medium 16 and (2) luminescent electromagnetic radiation 26 that is luminesced by luminescable medium 16 in response to radiation 13 received from emitter 12. For example, processor 18 may determine information about one or more gaseous analytes in the body of gas based on the relationship between the one or more gaseous analytes and the decay time of the luminescence of luminescable medium 16.

As is shown in FIG. 1, processor 18 includes a phase difference module 30, a delay compensation module 32, and an analyte information module 34. Modules 30, 32, and 34 may be implemented in software; hardware; firmware; some combination of software, hardware, and/or firmware; and/or otherwise implemented. It should be appreciated that although modules 30, 32, and 34 are illustrated in FIG. 1 as being co-located within a single processing unit, processor 18 may include multiple processing units, and that some of these processing units may be located remotely from each other. In such embodiments, one or more of modules 30, 32, and 34 may be located remotely from the other modules and operative communication between the modules may be achieved via one or more communication links. Such communication links may be wireless or hard wired.

Phase difference module 30 determines a phase difference between (1) a modulation of the amplitude of emitted amplified modulated electromagnetic radiation 13 from emitter 12 that becomes incident on luminescable medium 16 and (2) a modulation of the amplitude of received amplitude modulated electromagnetic radiation 26 luminesced by luminescable medium 16 in response to the emitted electromagnetic radiation 13.

In order to determine this phase difference, phase difference module 30 obtains the modulation of the amplitude of emitted electromagnetic radiation 13. In one embodiment, the modulation of the amplitude of emitted electromagnetic radiation 13 is obtained in the form of a periodic signal (e.g., a sinusoidal signal) that varies in proportion to, and/or with the frequency of, the modulation of the amplitude of emitted electromagnetic radiation 13. This signal may be obtained from a modulated power signal that is provided to emitter 12, from a modulated power signal used to drive an active optical element that modulates the amplitude of electromagnetic radiation 13 emitted by emitter 12, or from a signal related to the positioning of passive optical elements between emitter 12 and luminescable medium 16 to modulate the amplitude of electromagnetic radiation 13 provided to luminescable medium 16.

Phase difference module 30 also obtains the modulation of the amplitude of received electromagnetic radiation 26 that is luminesced by luminescable medium 16. In some embodiments, the modulation of amplitude of received electromagnetic radiation 26 that is luminesced by luminescable medium 16 is obtained in the form of a signal that varies in proportion to, and/or with the frequency of, the modulation of the amplitude of received luminescent electromagnetic radiation 26. For example, this signal may be obtained from the one or more output signals generated by photosensitive detector 14.

Phase difference module 30 determines a phase difference between the obtained modulation of amplitude of emitted electromagnetic radiation 13 and the obtained modulation of amplitude of received electromagnetic radiation 26. In some instances, phase difference module 30 includes a lock-in amplifier that generates a DC signal proportional to the phase difference between these two modulations of amplitude. In other instances, phase difference module 30 may be embodied in software that calculates the phase difference between the obtained amplitude modulations of radiation emitted 13 by emitter 12 and luminesced by luminescable medium 16.

Delay compensation module 32 compensates for one or more systems delays. For example, delay compensation module 32 compensates for the delay of photosensitive detector 14 in generating the one or more output signals discussed above. In one embodiment, delay compensation module 32 uses (1) the one or more output signals generated by photosensitive detector 14 that relate to an intensity (e.g., an amplitude) of luminescent radiation 26, and (2) a compensation curve that corresponds to photosensitive detector 14 and describes the delay as a function of the measured intensity of luminescence radiation 26 to determine the delay of photosensitive detector 14. For instance, the compensation curve may be of the form $D=a+b \cdot I+c/I$, as was described above with respect to the calibration of photosensitive detector 14. Once the delay is determined by delay compensation module 32, information that is being and/or has been processed by phase difference module 30 is adjusted by delay compensation module 32 to compensate for the determined delay.

For example, in one embodiment, delay compensation module 32 determines the delay of photosensitive detector 14 as a function of measured intensity (e.g., amplitude), and then adjusts the phase difference determined by phase difference module 30 to compensate for the delay determined by delay compensation module 32. In another embodiment, delay compensation module 32 uses the determined delay to adjust the amplitude modulation of luminescent electromagnetic radiation 26 that is obtained by phase difference module 30. In this embodiment, phase difference module 30 uses the adjusted amplitude modulation of luminescent electromagnetic radiation 26 (as adjusted by delay compensation module 32) to determine the phase difference between the amplitude modulation of electromagnetic radiation 13 from emitter 12 that is incident on luminescable medium 16 and the amplitude modulation of electromagnetic radiation 26 that is emitted by luminescable medium 16.

It should be appreciated that since luminescable medium 16 produces luminescent electromagnetic radiation 26 that is amplitude modulated (e.g., has periodic fluctuations in intensity), embodiments that compensate for a delay of photosensitive detector 14 as a function of measured intensity will be more accurate than embodiments that compensate for the delay as constant that does not depend on intensity. Therefore, the determination of the delay of photosensitive detector 14 as a function of measured intensity by delay compensation module 32, and the compensation performed to account for this delay will enhance an accuracy of processor 18 in determining a value of the phase difference between the amplitude modulation of electromagnetic radiation 13 emitted by emitter 12 onto luminescable medium 16 and the amplitude modulation of luminescent electromagnetic radiation 26.

Analyte information module 34 determines information related to one or more analytes in the body of gas within conduit 22 based on the phase difference between the amplitude modulation of electromagnetic radiation 13 from emitter 12 that is incident on luminescable medium 16 and the amplitude modulation of electromagnetic radiation 26 that is emitted by luminescable medium 16, as determined by phase difference module 30 and delay compensation module 32. For example, the phase difference determined by phase difference module 30 (as adjusted by delay compensation module 32) is related to the decay time of the luminescence of luminescable material 16. As was mentioned above, the decay time of luminescable material 16 varies as a function of an amount of one or more gaseous analytes present at luminescable medium 16. Therefore, analyte information module 34 is able to determine information related to these one or more gaseous analytes (e.g., an amount present at luminescable material 16) based on the phase difference determined by phase difference module 30 (as adjusted by delay compensation module 32). For example, analyte information module 34 may determine a concentration, a partial pressure, and/or other information related to the one or more gaseous analytes. In some embodiments, the one or more gaseous analytes may include oxygen.

Figure 4:
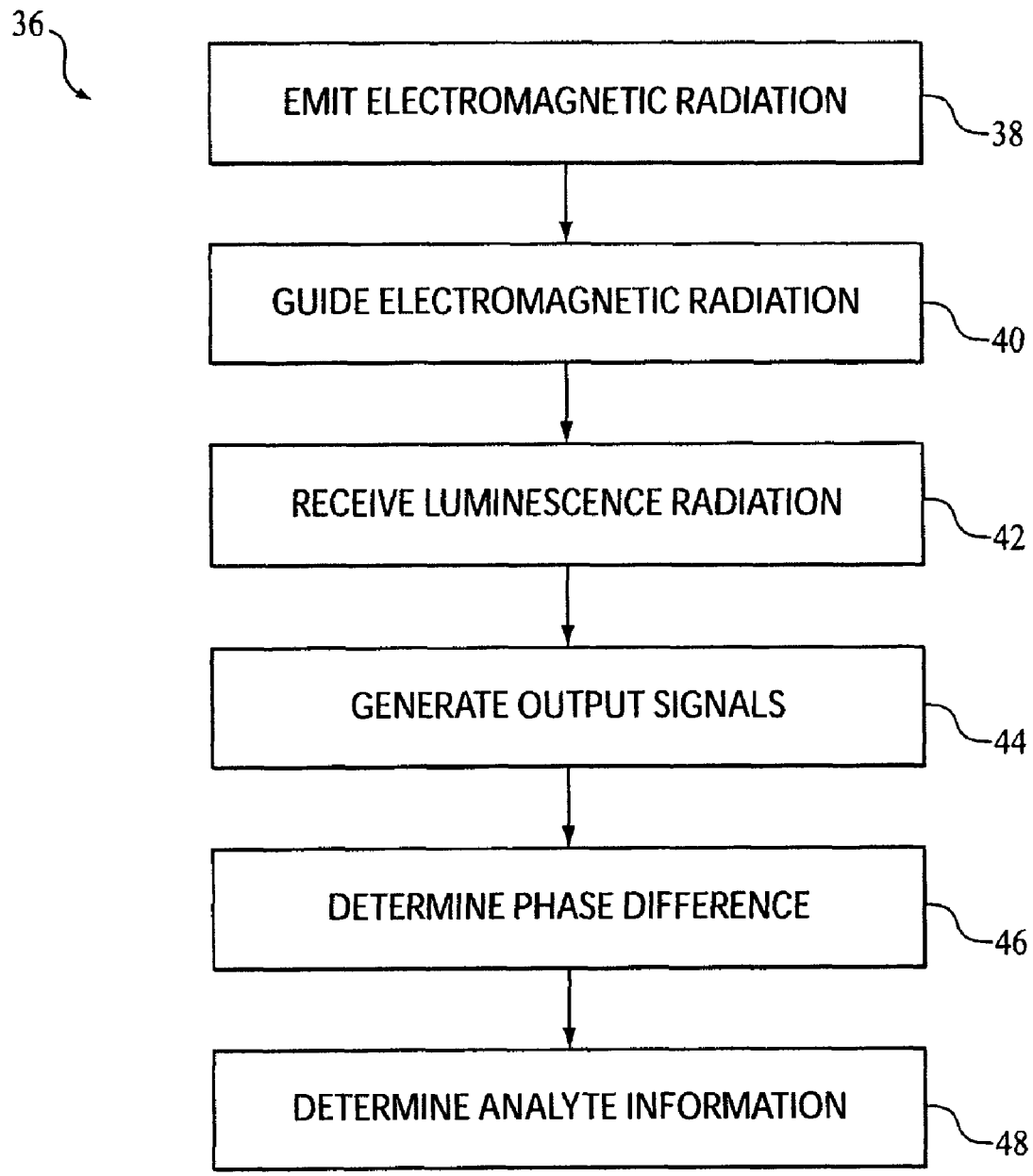
FIG. 4 illustrates a method of determining information related to one or more gaseous analytes in a body of gas, in accordance with one embodiment of the invention.

FIG. 4 illustrates a method 36 of determining information related to one or more gaseous analytes in a body of gas. At an operation 38, amplitude modulated electromagnetic radiation is emitted. The amplitude modulated electromagnetic radiation is emitted with one or more properties that will cause a predetermined luminescable medium to luminesce. For example, in one embodiment, operation 38 may be performed by emitter 12 in system 10 (as shown in FIG. 1).

At an operation 40, the emitted electromagnetic radiation is guided onto a luminescable medium disposed in a body of gas. The electromagnetic radiation guided to the luminescable medium causes the luminescable medium to luminesce, thereby emitting luminescent radiation. Because the electromagnetic radiation guided to the luminescable medium is amplitude modulated, the luminescent radiation is also amplitude modulated. As an example, operation 40 may guide radiation onto luminescable medium 16 of system 10 (as shown in FIG. 1).

At an operation 42, the luminescent radiation emitted by the luminescable medium is received. At an operation 44 one or more output signals are generated. At least one of the output signals indicates an intensity of the luminescent radiation received from the luminescable medium. In one embodiment, operations 42 and 44 are performed by photosensitive detector 14 of system 10 (as shown in FIG. 1).

At an operation 46, a phase difference between the amplitude modulation of the electromagnetic radiation that is guided to the luminescable medium and the amplitude modulation of the luminescent radiation that is emitted by the luminescable medium is determined. At operation 46, the phase difference is determined to compensate for a delay in the generation of the output signals that varies as a function of the intensity of the luminescent radiation. In some embodiments, operation 46 is performed by processor 18 of system 10 (as shown in FIG. 1) as set forth previously.

At an operation 48, information related to one or more gaseous analytes in the body of gas are determined based on the phase difference determined at operation 46. In one embodiment, the information determined at operation 48 may include information related to an amount of the one or more gaseous analytes, such as a partial pressure, a concentration, or other information. In some embodiments, operation 48 is performed by processor 18 of system 10 (as shown in FIG. 1) as described above.

Figure 5:
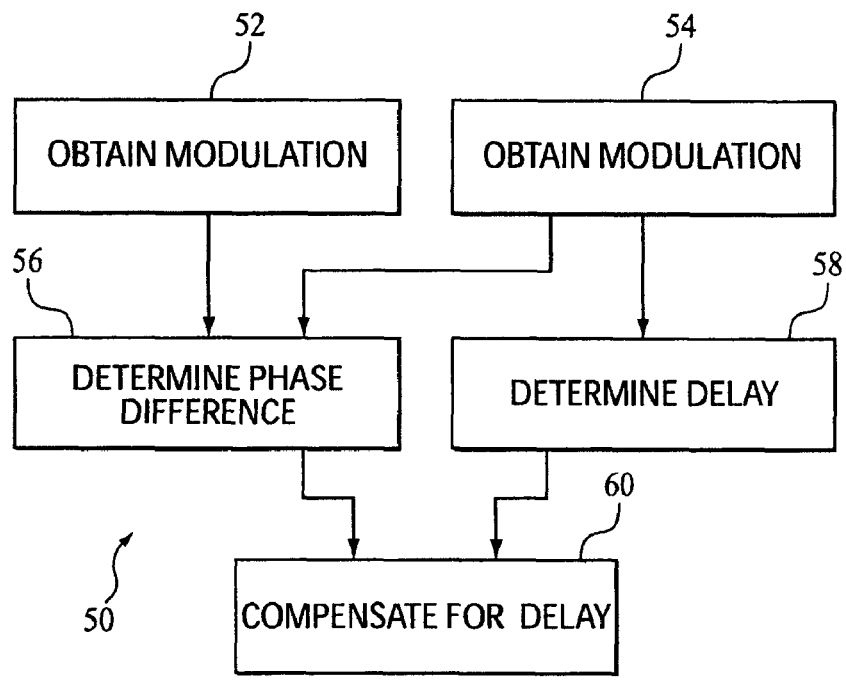
FIG. 5 illustrates a method of compensating for a non-constant system delay, in accordance with one embodiment of the invention.

FIG. 5 illustrates a method 50 of determining a phase difference between the amplitude modulation of electromagnetic radiation that is guided to a luminescable medium and the amplitude modulation of electromagnetic radiation that is luminesced by the luminescable medium in response to the received radiation. In one embodiment, some or all of the operations of method 50 are executed at operation 46 of method 40 (as shown in FIG. 4)

At an operation 52, the amplitude modulation of the electromagnetic radiation that is guided to the luminescable medium is obtained. This includes obtaining the magnitude of the amplitude, or intensity, of the radiation as a function of time. In one embodiment, operation 52 may be performed by phase difference module 30 (as shown in FIG. 1), as was described above.

At an operation 54, the amplitude modulation of the electromagnetic radiation that is luminesced by the luminescable medium is obtained. In one embodiment, the amplitude modulation of this luminescent electromagnetic radiation is obtained from the output signal(s) of a photosensitive detector that receives the luminescent radiation. For instance, operation 54 may be performed by phase difference module 30 obtaining the one or more output signals generated by photosensitive detector 14 (as shown in FIG. 1) in the manner set forth above.

At an operation 56, the phase difference between the obtained amplitude modulation of the electromagnetic radiation guided to the luminescable medium and the obtained amplitude modulation of the electromagnetic radiation luminesced by the luminescable medium is determined. The phase difference may be determined by adding, subtracting, and/or demodulating these amplitude modulations. In one embodiment, operation 56 may be executed by phase difference module 30 (as shown in FIG. 1), as discussed above.

At an operation 58, a delay in the generation of the output signal(s) used at operation 54 to obtain the amplitude modulation of the electromagnetic radiation luminesced by the luminescable medium is determined. At operation 58, the delay is determined as a function of the amplitude, or intensity, of the electromagnetic radiation luminesced by the luminescable medium. In one embodiment, operation 58 is executed by phase delay module 32 (as shown in FIG. 1) in the manner described previously. In some instances, a compensation for the delay may be determined at operation 58, instead of the actual delay.

At an operation 60, the phase difference determined at operation 56 is adjusted to compensate for the delay determined at operation 58. This will enhance accuracy and/or a precision of the phase difference. In one embodiment, the compensation for the delay includes either adding or subtracting the delay determined at operation 58 from the phase difference determined at operation 56. In some instances, operation 60 may be performed by delay compensation module 32 and/or phase difference module 30 (as shown in FIG. 1).

Figure 6:
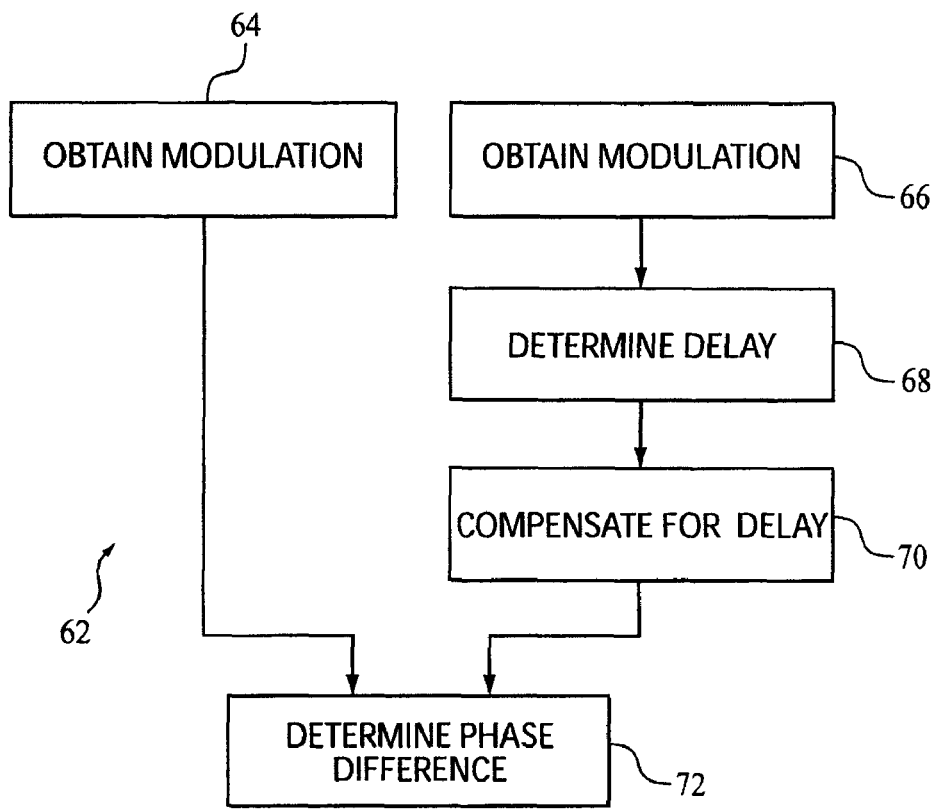
FIG. 6 illustrates an alternate method of compensating for a non-constant system delay, in accordance with one embodiment of the invention.

FIG. 6 illustrates one possible alternative method 62 of determining a phase difference between the amplitude modulation of electromagnetic radiation that is guided to a luminescable medium and the amplitude modulation of electromagnetic radiation that is luminesced by the luminescable medium in response to the received radiation. As with method 50, in some embodiments, some or all of the operations of method 62 are executed at operation 46 of method 36 (as shown in FIG. 4).

At an operation 64, the amplitude modulation of the electromagnetic radiation that is guided to the luminescable medium is obtained. This includes obtaining the magnitude of the amplitude, or intensity, of the radiation as a function of time. In one embodiment, operation 64 corresponds to operation 52 of method 50, as illustrated in FIG. 5 and described above.

Returning to FIG. 6, at an operation 66, the amplitude modulation of the electromagnetic radiation that is luminesced by the luminescable medium is obtained. In one embodiment, the amplitude modulation of the luminescent electromagnetic radiation is obtained from the output signal(s) of a photosensitive detector that receives the luminescent radiation. Operation 66 may correspond to operation 54 of method 50, as illustrated in FIG. 5 and set forth previously.

At an operation 68 in FIG. 4, a delay in the generation of the output signal(s) used at operation 66 to obtain the amplitude modulation of the electromagnetic radiation luminesced by the luminescable medium is determined. At operation 68, the delay is determined as a function of the amplitude, or intensity, of the electromagnetic radiation luminesced by the luminescable medium. In one embodiment, operation 68 corresponds to operation 58 of method 50, as described above. As was the case with operation 58, in some instances, a compensation for the delay may be determined at operation 68, instead of the actual delay.

At an operation 70, an adjusted amplitude modulation of the electromagnetic radiation that is luminesced by the luminescable medium is determined. This includes adjusting the amplitude modulation determined at operation 66 to compensate for the delay determined at operation 68. In some embodiments, operation 70 may be executed by phase delay module 32 (as shown in FIG. 1), as was described above.

At an operation 72, a phase difference is determined for the adjusted amplitude modulation determined at operation 70 and the amplitude modulation of electromagnetic radiation guided to the luminescable medium determined at operation 64. The phase difference may be determined by adding, subtracting, and/or demodulating these amplitude modulations. In one embodiment, operation 72 may be executed by phase difference module 30 (as shown in FIG. 1), as discussed above.

In the embodiments of the invention described above and as illustrated in FIGS. 4-6, the compensation for the system delay caused by photosensitive detector 14 has been made to information to provide a compensated determination of the phase differences between the amplitude modulation of electromagnetic radiation 13 directed to luminescable medium 16 and the amplitude modulation of luminescent radiation 26. However, other mechanisms of compensating for the system delay are contemplated. In one embodiment, the actual information related to the one or more analytes determined by analyte information module 24 is compensated based on the system delay after it has been determined. For example, in this embodiment analyte information module 24 may determine an uncompensated concentration of an analyte and delay compensation module 32 may adjust the determined concentration. In another embodiment, the obtained value of the amplitude modulation of electromagnetic radiation 13 that is guided to luminescable medium 16 may be adjusted to account for the system delay of the sensor. In this embodiment, the adjustment of the obtained amplitude modulation of electromagnetic radiation 13 that is guided to luminescable medium 16 would be adjusted prior to determining a phase difference between this amplitude modulation and the amplitude modulation of the electromagnetic radiation 26 that is luminesced by the luminescable medium 16.

It should be appreciated that although the system and methods described above have been set forth in the context of analyzing gaseous analytes, the general principles of the invention are more far reaching. For instance, the principles of adjustment for system delays in luminescent detectors as a function of luminescent illumination intensity may be extended to other types of detectors and/or analyzers that rely on the detection of decay times of luminescent illumination.

Other embodiments, uses and advantages of the invention will be apparent to those skilled in the art from consideration of the specification and practice of the invention disclosed herein. The specification should be considered exemplary only, and the scope of the invention is accordingly intended to be limited only by the following claims.

What is claimed is:

1. A system configured to determine information related to one or more gaseous analytes in a body of gas, the system comprising:
    a luminescable medium in communication with the body of gas;
    one or more emitters configured to emit electromagnetic radiation onto the luminescable medium, wherein the emitted electromagnetic radiation causes luminescence in the luminescable medium;
    a photosensitive detector configured to receive electromagnetic radiation that is generated by luminescence of the luminescable medium, wherein the photosensitive detector generates one or more output signals in response to the received electromagnetic radiation, the one or more output signals indicating an intensity of the received electromagnetic radiation; and
    a processor adapted to receive the one or more output signals generated by the photosensitive detector and adapted to determine the information related to one or more gaseous analytes in the body of gas based on a phase difference between the emitted electromagnetic radiation and the received amplitude modulated electromagnetic radiation,
    wherein the processor is further adapted to determine a detector delay of the photosensitive detector in the generation of the one or more output signals and compensate the phase difference for the determined detector delay.

2. The system of claim 1, wherein the one or more gaseous analytes comprises oxygen.

3. The system of claim 1, wherein the information related to the one or more gaseous analytes comprises concentrations of the one or more gaseous analytes in the body of gas.

4. The system of claim 1, wherein the processor comprises a phase difference module adapted to determine the phase difference between the emitted electromagnetic radiation and the received electromagnetic radiation.

5. The system of claim 4, wherein the phase difference module comprises a lock-in amplifier.

6. The system of claim 4, wherein the processor is adapted to (i) determine the detector delay of the photosensitive detector in the generation of the one or more output signals based on the intensity of the received electromagnetic radiation as indicated by the one or more output signals, and (ii) compensate, based on the determined detector delay, for the detector delay of the photosensitive detector in the generation of the one or more output signals by adjusting the phase difference determined by the phase difference module.

7. The system of claim 1, wherein the processor is adapted to control the one or more emitters.

8. A method of determining information related to one or more gaseous analytes in a body of gas, the method comprising the acts of:
   providing an emitted electromagnetic radiation onto a luminescable medium in communication with the body of gas so as to cause luminescence in the luminescable medium;
   receiving by a detector an electromagnetic radiation, wherein the received electromagnetic radiation is generated by the luminescence of the luminescable medium;
   generating by the detector one or more output signals indicating an intensity of the received electromagnetic radiation received from the luminescable medium;
   determining a phase difference between the emitted electromagnetic radiation and the received electromagnetic radiation;
   compensating the phase difference for a detector delay between receipt of the received electromagnetic radiation by the detector and the generation of the one or more output signals by the detector; and
   determining the information related to one or more gaseous analytes in the body of gas based on the compensated phase difference.

9. The method of claim 8, wherein the one or more gaseous analytes comprises oxygen.

10. The method of claim 8, wherein the determining the information act comprises determining concentrations of the one or more gaseous analytes in the body of gas.

11. The method of claim 8, wherein the compensating act includes adjusting the one or more output signals of the detector based on the determined delay, and using the adjusted one or more output signals to determine the compensated phase difference.

12. The method of claim 8, further comprising the act of emitting the emitted amplitude modulated electromagnetic radiation.

13. A processor configured to determine information related to one or more gaseous analytes in a body of gas, the processor comprising:
   a phase difference module adapted to determine a phase difference between (i) an emitted electromagnetic radiation that has been provided to a luminescable medium in communication with the body of gas and (ii) a received electromagnetic radiation generated by luminescence of the luminescable medium in response to the emitted electromagnetic radiation provided thereon,
   wherein the phase difference module is adapted to determine the phase difference based on one or more output signals generated by a photosensitive detector, wherein the photosensitive detector is structured to receive at least a portion of the received electromagnetic radiation generated by the luminescence of the luminescable medium and structured to generate the one or more output signals, and wherein at least some of the output signals indicate an intensity of the received electromagnetic radiation generated by the luminescence of the luminescable medium;
   a delay compensation module adapted to provide a compensation of the phase difference for a detector delay of the photosensitive detector in generating the one or more output signals; and
   an analyte information module adapted to determine the information related to one or more gaseous analytes in the body of gas based on the compensated phase difference.

14. The processor of claim 13, wherein the one or more gaseous analytes comprises oxygen.

15. The processor of claim 13, wherein the information related to the one or more gaseous analytes determined by the processor comprises concentrations of the one or more gaseous analytes in the body of gas.

16. The processor of claim 13, wherein the phase difference module comprises a lock-in amplifier.

17. The processor of claim 13, wherein the delay compensation module is further adapted to (i) determine the delay of the photosensitive detector in the generation of the one or more output signals based on the intensity of the electromagnetic radiation, wherein the intensity is indicated by the one or more output signals, and (ii) compensate for the delay of the photosensitive detector in the generation of the one or more output signals by adjusting the phase difference determined by the phase difference module based on the determined delay.

18. The processor of claim 13, wherein the delay compensation module is further adapted to (i) determine the delay of the photosensitive detector in the generation of the one or more output signals based on the intensity of the received electromagnetic radiation, wherein the intensity is indicated by the one or more output signals, and (ii) compensate for the delay of the photosensitive detector in the generation of the one or more output signals by adjusting the one or more output signals to account for the delay, and wherein the phase difference module is further adapted to determine the phase difference based on the output signals that have been adjusted by the delay compensation module.

19. A method of determining information on a gaseous analyte in a body of gas, comprising the acts of:
   determining a phase difference between (i) an emitted electromagnetic radiation provided to a luminescable medium in communication with the body of gas and (ii) output signals from a detector that receives a received amplitude modulated electromagnetic radiation generated by the luminescence of the luminescable medium;
   compensating the phase difference for a detector delay of the detector in generation of the output signals; and
   determining the information related to the gaseous analyte based upon the compensated phase difference.

20. The system of claim 1, wherein the detector delay is obtained from a curve of measured detector delays and measured intensities obtained during calibration measurements.

21. The system of claim 1, wherein the detector delay is obtained from a look-up table of measured detector delays and measured intensities obtained during calibration measurements.

22. The system of claim 1, wherein the processor is further adapted to compensate the phase difference by adjusting the one or more output signals of the detector based on the determined detector delay, and to use the adjusted one or more output signals to determine the compensated phase difference.

23. The system of claim 1, wherein the detector delay varies as a function of the intensity of the received amplitude modulated electromagnetic radiation received by the photosensitive detector; and the compensation varies as the function of the intensity of the received amplitude modulated electromagnetic radiation.

* * * * *